(12) United States Patent
Hollander et al.

(10) Patent No.: US 9,539,364 B2
(45) Date of Patent: Jan. 10, 2017

(54) CELL BANDAGE

(75) Inventors: Anthony P. Hollander, Bristol (GB); Wa'el Z. Kafeinah, Bristol (GB); Ehsanollah Esfandiari, Harpendon (GB); John F. Tarlton, Bristol (GB)

(73) Assignee: The University of Bristol (GB)

( * ) Notice: Subject to any disclaimer, the term of this patent is extended or adjusted under 35 U.S.C. 154(b) by 2073 days.

(21) Appl. No.: 11/663,582

(22) PCT Filed: Sep. 23, 2005

(86) PCT No.: PCT/GB2005/003690
§ 371 (c)(1),
(2), (4) Date: Dec. 6, 2007

(87) PCT Pub. No.: WO2006/032915
PCT Pub. Date: Mar. 30, 2006

(65) Prior Publication Data
US 2008/0199429 A1    Aug. 21, 2008

(30) Foreign Application Priority Data
Sep. 24, 2004   (GB) .................. 0421298.1

(51) Int. Cl.
*C12N 5/00* (2006.01)
*A61K 9/70* (2006.01)
*A61L 27/38* (2006.01)
*A61L 27/36* (2006.01)
*A61L 31/00* (2006.01)

(52) U.S. Cl.
CPC ........ *A61L 27/3817* (2013.01); *A61L 27/3612* (2013.01); *A61L 27/3641* (2013.01); *A61L 27/3645* (2013.01); *A61L 27/3843* (2013.01); *A61L 31/005* (2013.01)

(58) Field of Classification Search
CPC ............ C12N 5/06; C12N 5/0655; A61K 9/70
USPC ........................................ 424/400; 435/325
See application file for complete search history.

(56) References Cited

U.S. PATENT DOCUMENTS

| 6,444,222 B1 * | 9/2002 | Asculai et al. ............... 424/484 |
| 2002/0110544 A1 * | 8/2002 | Goldberg et al. ............ 424/93.7 |
| 2004/0096505 A1 | 5/2004 | Woerly |

FOREIGN PATENT DOCUMENTS

WO     WO 00/48550 A    8/2000

OTHER PUBLICATIONS

Peretti GM et al,: Cell Based Therapy for Meniscal Repair: A Large Animal Study Am. J. Sports Med. 2004, 32: 146.

* cited by examiner

*Primary Examiner* — Ruth Davis
(74) *Attorney, Agent, or Firm* — Bryan D. Zerhusen; Locke Lord LLP

(57) ABSTRACT

The invention provides a method for delivering cells across the surface of a tissue, the method comprising distributing the cells on and/or within a sheet of biomaterial to form a cell bandage and applying the cell bandage to the surface, wherein, after application of the cell bandage to the surface of the tissue, the cells are released from the cell bandage. Further provided is a method for bonding two or more tissues, the method comprising providing a cell bandage in intimate contact with the surfaces to be joined, wherein the cell bandage comprises a sheet of biomaterial, said biomaterial having cells distributed on and/or within it. Also provided is a cell bandage for use in the methods of the invention.

18 Claims, 16 Drawing Sheets

Figure 16

CELL BANDAGE

This application is the U.S. national phase application, pursuant to 35 U.S.C. §371, of PCT international application Ser. No. PCT/GB2005/003690, filed Sep. 23, 2005, designating the United States and published in English on Mar. 30, 2006 as publication WO 2006/032915 A2, which claims priority to Great Britain application Ser. No. GB 0421298.1, filed Sep. 24, 2004. The entire contents of all of the aforementioned patent applications are incorporated herein by this reference.

This invention relates generally to the treatment or repair of damaged tissues.

The present invention will be described with reference to its preferred embodiment as a method for directing cells across and into cartilaginous tissue. However, the present invention finds equal utility in other tissue engineering applications where controlled cell distribution across a tissue surface is required.

Articular cartilage lines the ends of articulating bones in diarthroidal joints of the body. It is composed of collagen fibrils, a proteoglycan matrix and chondrocytes (the cells that produce cartilage matrix). Mature articular cartilage has a limited capacity for regeneration after degeneration or injury. Lesions within mature articular cartilage are generated during the course of many joint diseases, notably osteoarthritis (OA), traumatic damage and osteochondritis dissecans (Hunziker, 2002). Traumatic lesions may occur directly or indirectly in consequence of an intraarticular fracture, a high-intensity impact or following ligament injuries (Buckwalter et al., 1998). Articular cartilage lesions generally do not heal, or heal only partially under certain biological conditions. They are frequently associated with disability and with symptoms such as joint pain, locking phenomena and reduced or disturbed function. Moreover, such lesions are generally believed to progress to severe forms of OA (Gilbert, 1998; Hunziker, 2002).

The numerous experimental and clinical attempts that have been made to induce the healing of histologic and macroscopic lesions within mature articular cartilage aim at re-establishing a structurally and functionally competent repair tissue of an enduring nature.

There are two major biological problems associated with articular cartilage repair. The first problem is the construction of repair tissue with the same structural and mechanical properties as articular cartilage (Shapiro et al., 1993). The second problem is to achieve successful integration across the interface between the host and repair tissue.

An important prerequisite for long-term repair or regeneration of articular cartilage is the integration of transplanted cartilage or locally induced repair tissue with the native cartilage at the recipient site (Ahsan et al., 1999; Hunziker, 1999). Integrative cartilage repair is probably hindered by the lack of matrix-producing cells in the cartilage-cartilage interface area (Ahsan et al., 1999; Reindel et al., 1995). The acellularity is due to a combination of chondrocyte loss from lesion edges, avascularity, or the absence of multipotent progenitor cells.

Current methods used in the clinic to encourage natural cartilage repair include debridement, subchondral drilling or microfracture and mosaicoplasty. Such techniques usually results in fibrocartilagenous repair tissue that fails mechanically with time. More importantly, there is no way to monitor the quality of the repair tissue generated.

Autologous chondrocyte implantation (ACI) is the first generation of cell based therapy of articular cartilage defects. It is based on expanding autologous articular chondrocytes taken from non-weight bearing area and implanting them into a defect under a periosteal or collagen flap (Gillogly, 2003). The object is to keep the implanted cells in place until they can form cartilage.

The second generation of cartilage tissue engineering involves using biodegradable scaffolds seeded with expanded chondrocytes to create a an immature, implantable construct that can fill the defect.

However, ACI and immature constructs can only be used to treat confined defects. These procedures are not suitable for treatment of the unconfined lesions that are typical of osteoarthritis, a degenerative joint disease involving the loss of articular cartilage. For better treatment of unconfined lesions it is desirable to have a "sheet" of ready-formed mature cartilage to resurface the entire lesion. Accordingly, there is an interest in engineering mature cartilage tissue in vitro in order to produce mature, functionally- and mechanically-sound implants ready to fill cartilage defects such as those caused by osteoarthritis.

Once positioned over the lesion, it is necessary that the engineered mature cartilage integrates with the existing cartilage surrounding the lesion to form a unified tissue which provides a durable articular surface. Integration of the repair tissue with surrounding native cartilage is a critical step in the development of cartilage tissue engineering strategies. Initial, temporary fixation of an engineered cartilage implant may be achieved using sutures or fibrin glue. However there will be a clear discontinuity between the implant and host cartilage, creating a focus for failure (Hunziker, 1999). There is no clear evidence in the literature demonstrating that integration of adjacent surfaces in vivo occurs either readily or consistently. This can be explained by the poor environment of the defect characterised by collagen fibrillation and fissure formation (Donohue et al., 1983; Thompson et al., 1991). Furthermore, blunt trauma was shown to cause apoptosis of chondrocytes of the defect walls (Redman et al., 2004).

The present inventors hypothesise that in order to achieve a continuous matrix, cells with the capacity to synthesise cartilage must migrate between the implant and host tissue. Chondrocytes residing within the lacunae of natural or engineered cartilage are unlikely to migrate in this way. Previous studies have proposed coating the surface of engineered cartilage with isolated chondrocytes (Peretti et al., 1999; Peretti et al., 2003; Schinagl et al., 1999). It was initially supposed that these cells would create a bridge between the transplant and the surrounding cartilage. More recent observations suggest that the chondrocytes actually act to break down neighbouring cartilage and regenerate new cartilage tissue. However, this strategy had limited success because it was found that the chondrocytes coating the transplant have a tendency to aggregate into clumps with the result that discreet "mini-bridges" are formed between the implant and the surrounding tissue. These mini-bridges do not form a sufficiently strong bond between the implant and surrounding tissues for the repaired cartilage to withstand the mechanical stresses to which it is subjected in the joint.

The present inventors realised that the key to achieving improved integration of implanted cartilage with native cartilage at the recipient site is to find a method for delivering cells across a surface and, once in position, releasing them.

Accordingly, in a first aspect, the invention provides a method for delivering cells across the surface of a tissue, the method comprising distributing the cells on and/or within a sheet of biomaterial to form a cell bandage and applying the cell bandage to the surface, wherein, after application of the cell bandage to the surface of the tissue, the cells are released from the cell bandage so that they are able to migrate through the biomaterial and into the neighbouring tissue.

As used herein, the term "cell bandage" is intended to mean any vehicle for applying cells in close apposition to the surface of a tissue which comprises cells distributed on or within a biomaterial. Conveniently, the cell bandage is in the form of a sheet.

As used herein, the term "biomaterial" means any substance (other than a drug), synthetic or natural, that can be used as a system or part of a system that treats, augments, or replaces any tissue, organ, or function of the body. Preferably, the biomaterial is biodegradable, that is, it does not persist indefinitely in the body but is gradually broken down, although it is possible that there may be a residual presence. Any biomaterial can be used provided that the cells will adhere to it or can be held within it. Examples of suitable biomaterials include PGA, PGLA and chitosan. In addition to synthetic biomaterials, natural biomaterials such as collagen may also be used, as illustrated herein. The biomaterial may be a scaffold or a non-solid support (gel-like) such as a suspension of fibres provided that the biomaterial can be held in place and that it persists long enough for the cells to grow/develop. A scaffold may be held in place e.g. by a suture and has a relatively long half-life. The biomaterial may be inherently sticky which helps to retain the cell bandage in the desired position. The primary function of the biomaterial is as a physical carrier although it could potentially also provide a biological stimulus e.g. by utilising a material that can signal to cells.

The following description refers to surgical "implantation" and "transplantation" of tissues, especially cartilage. Implantation is intended to refer to the surgical introduction of engineered tissue grown outside the body (an "implant") whereas transplantation is intended to refer to the surgical introduction of tissue transferred from elsewhere in the body (a "transplant"). The transplant may originate from the patient or from a donor. The invention has general application irrespective of how the tissue is derived. Accordingly, any reference herein to transplanted tissues may be taken to apply equally to implanted tissues and vice versa.

In a second aspect, the invention provides a method for bonding two or more tissues, the method comprising providing a cell bandage in intimate contact with the surfaces to be joined, wherein the cell bandage comprises a sheet of biomaterial, said biomaterial having cells distributed on and/or within it. Preferably, the cell bandage is provided at the interface between the tissues to be joined.

Preferably, the cells are cartilage producing cells, or cells capable of producing cartilage, such as chondrocytes, chondro-progenitor cells or stem cells and the tissue or tissues is/are cartilaginous. Examples of suitable chondrocytes are chondrocytes obtained from articular cartilage, meniscus or nasal cartilage. An example of suitable stem cells is human bone marrow mesenchymal stem cells. Preferably, the cells are evenly distributed throughout the volume of the cell bandage, or over the entire surface of each side of the cell bandage, in order that cartilage producing cells are presented to the neighbouring tissue in a uniform fashion across the whole of the interface between the cell bandage and the surface of each of the tissues to be joined. In this way, migration of cartilage producing cells from the cell bandage into each of the neighbouring tissues is facilitated, producing continuous integration at the interface across the entire surface.

In a preferred embodiment of the invention, the cell bandage comprises chondrocytes, chondro-progenitor cells or stem cells and is used to integrate one cartilaginous tissue with another. Preferably, the cells have been isolated from the patient to be treated. The cells may be from the same source as that used to produce engineered cartilage, or from a generic source such as any matrix cell type or other cell type. In the repair of osteoarthritic lesions in articular cartilage, the cell bandage may be used to integrate surgically implanted engineered cartilage, or native cartilage transplanted from a donor tissue, with adjacent native cartilage at the recipient site. Because the cell bandage is in the form of a sheet, the implant or transplant may, for example, be wrapped in the cell bandage prior to implantation or the cell bandage may be laid in the lesion prior to implantation. The implant and cell bandage are held in place e.g. by a suture. If the implant is wrapped in the cell bandage, the cell bandage acts to secure the implant in place as well as to distribute the chondrocytes or other cells across the surfaces of the implant and the native tissue adjacent the lesion. The sheet conforms to the shape of the implant/transplant and the tissue adjacent the lesion, thereby holding the cells in close apposition to the opposing tissue surfaces. The sheet can completely fill the gaps between the implant and the host tissue and thus allows controlled delivery of actively dividing cells to the cartilage-cartilage interface. The method allows uniform development of new cartilage across the opposing surfaces and enables continuous integration of the implant and the surrounding tissue across the whole interface between the two tissues, thus providing a biomechanically stable tissue and a durable articular surface.

The cell bandage provides a mechanism for the controlled delivery of actively dividing cells, which have the capacity to synthesize cartilage, to the cartilage-cartilage interface. As shown in the examples, the cell bandage achieves closure of the interstitial space by providing cartilage producing cells which migrate into each of the tissues to be bonded (joined), thus producing effective integration. The inventors hypothesise that the cell bandage provides a source of cartilage producing cells which are able to degrade the matrix of the surrounding cartilage and migrate into it, synthesizing new cartilage to fill the space through which they have migrated, thus producing a continuous matrix. The present invention may, therefore, be characterised as space-closing, wherein the tissue surfaces to be joined are effectively integrated with one another by migration of cartilage producing cells from the cell bandage into each of the neighbouring tissues, followed by biodegradation of the biomaterial support component of the cell bandage, as opposed to space-filling, wherein new tissue is generated to fill the space between the surfaces of the neighbouring tissues. The space-closing action of the present invention provides a continuous matrix integrating each of the tissues to be joined with its neighbour, resulting in a repair with greater mechanical stability (durability) than space-filling repair strategies of the prior art which merely produce new tissue to fill a void created by degeneration or injury.

It will be understood that in order to fully effect the space-closing outcome of the invention, the cartilage producing cells released from the cell bandage will not only migrate into the neighbouring tissues where they will regenerate cartilage, they will also migrate within the biomaterial scaffold of the cell bandage as it degrades, regenerating cartilage. In this way, a continuous matrix is formed across the adjoining tissue surfaces.

Preferably the cell bandage is relatively thin. Preferably, it is less than 1.0 mm thick. More preferably, the cell bandage is less than 0.9 mm, 0.8 mm, 0.7 mm, 0.6 mm, 0.5 mm or 0.4 mm thick, in increasing order of preference. The physical properties of the biomaterial will determine the minimum thickness, beyond which the integrity of the bandage is compromised by lack of strength. A cell bandage with a thickness of 0.5 mm has been found to have desirable properties. The space-filling tissue repair strategies of the prior art require relatively thick scaffolds to occupy the void created by the lesion and retain cells during matrix generation. In contrast, the space-closing method of the invention requires a relatively thin sheet of biomaterial so that, following migration of cartilage producing cells into the neighbouring tissues (e.g. implant and native cartilage), the biomaterial is readily degraded and there is a substantially continuous integration of the tissues to be joined. Ideally, the cell bandage itself gradually degrades to be replaced by integrating tissue.

Preferably, the biomaterial of the cell bandage has an open structure at the surface abutting the tissue with which it is to integrate, for example, in the case of a collagen membrane, the "weave" of the collagen fibres at the surface is relatively loose so as to allow the collagen producing cells seeded onto the membrane to migrate easily into the neighbouring tissue. At the microscopic level, an open, loose scaffold like this has a "rough" appearance and, in the examples which follow is termed a rough surface. Commercially available biomaterial scaffolds possess specific physical characteristics consistent with the use for which they are designed. For example, the collagen membrane available from "Geistlich" has a "rough" surface and a "smooth" surface. At the microscopic level, the collagen fibres at the rough surface are less tightly packed and provide an open structure of fibres in varying orientations with spaces between. In contrast, at the smooth surface, the fibres are more densely packed and lie parallel to the surface. A membrane with one rough surface and one smooth surface is suited to autologous chondrocyte implantation therapy, wherein the purpose of the collagen membrane is to keep the implanted cells in place. The smooth surface of the membrane acts as a barrier to prevent escape of cells from the lesion to be repaired.

The present inventors have found that the open structure of the rough surface allows the cartilage producing cells in the cell bandage to migrate more readily from the cell bandage into the surrounding tissue. The degree of openness of the biomaterial structure, apparent as the roughness of the surface, is, therefore, a controlling factor for integration. Preferably, therefore, the cell bandage has a rough surface at its interface with each of the surfaces to be joined, thus presenting cartilage producing cells at each surface of the bandage and allowing ready migration of cartilage producing cells into the neighbouring tissues and enabling effective integration right across the interface of the tissues to be joined.

The inventors' results using a hyaline cartilage model system indicate that, for the space-closing objective of the method of the invention, the ideal properties of the biomaterial for the cell bandage are that it should be relatively thin so as to minimise as far as possible the gap between the tissues to be joined and that its structure should be sufficiently adhesive to retain cartilage producing cells which have been seeded onto it up to implantation, but not so strongly adhesive that migration of cells from the cell bandage into the neighbouring tissues is prevented. In other words, the biomaterial is adapted, physically or chemically, to allow rapid release of cells into the tissue following implantation. The rate of release of cells from the cell bandage may be tailored to suit particular applications. Appropriate properties are shown by the rough surface of the Geistlich collagen membrane.

Preferably, the biomaterial sheet of the cell bandage has cells on and/or within it at both surfaces and is rough on both surfaces so that cells able to migrate into the tissues to be joined are presented at the interface with each of the tissues to be joined.

Although the invention is described above with reference to a preferred embodiment as a method for integrating implanted or transplanted cartilage in the repair of osteoarthritic lesions, it will be apparent to the person skilled in the art that the invention is equally applicable in the repair of damaged cartilage arising from other diseases or injuries.

The cell bandage may also be used to integrate two or more pieces of engineered cartilage to form unified pieces of engineered cartilage of a greater size than can otherwise be grown in vitro. The size of cartilage tissue that can be grown in vitro is limited by mass transfer limitations meaning that, once a piece of tissue reaches a certain size, it is no longer possible for cells at the centre to exchange nutrients (e.g. oxygen) and waste products with the surrounding medium. Using the cell bandage of the invention, it is possible to overcome this limitation by taking multiple small pieces of engineered cartilage and inducing them to integrate with one another to form a larger sheet in the manner of a jigsaw puzzle by wrapping them in cell bandage. The composite cartilage thus formed may then be applied together with the cell bandage of the invention to repair a lesion in articular cartilage. Alternatively, multiple pieces of engineered cartilage may be implanted together with the cell bandage so that the pieces of engineered cartilage are integrated with one another and with the native cartilage at the same time, both occurring in vivo.

Another injury which may be repaired by the method of the invention is a meniscal tear. Meniscal cartilage occurs in the meniscus of the knee. A meniscal tear is a relatively common injury which is associated with an elevated risk of later development of osteoarthritis. This injury may be treated by laying a cell bandage over the tear and holding it in place e.g. by a suture. In this case, the two surfaces to be joined by the method arise from the same tissue: they are the inner surfaces created by the tear. The cell bandage may be sandwiched between the two surfaces (i.e. inserted into the tear). Alternatively, it may be sufficient that the cartilage producing cells are held in close apposition to the tear by the biomaterial support (e.g. fixed across the tear). The inventors have observed that cells from the cell bandage are able to infiltrate the adjacent cartilage tissue. Accordingly, it is thought that some cells from the biomaterial will infiltrate the area of the tear. In the same way, in the method for assembling composite engineered cartilage described above, the enveloping cell bandage may promote integration of the individual pieces of engineered cartilage without necessarily being arranged to lie between the surfaces to be joined, providing the cell bandage abuts the junction of the opposed surfaces.

In a further aspect, the invention provides a cell bandage which comprises a sheet of biomaterial, said biomaterial having cells distributed on and/or within it. Preferably, the cells are cartilage producing cells, or cells capable of producing cartilage, such as chondrocytes, chondro-progenitor cells or stem cells. Examples of suitable chondrocytes are chondrocytes obtained from articular cartilage, meniscus or nasal cartilage. An example of suitable stem cells is human bone marrow mesenchymal stem cells. Other preferred features of the cell bandage are as described in relation to the method of the invention. In a particularly preferred embodiment, the sheet of biomaterial has cells at or on both surfaces and the structure of the biomaterial is adapted to permit outward migration of cells from the bandage into the adjoining tissue, once the cell bandage is in place (e.g. for a collagen membrane, the membrane should be rough on both sides). Preferably, the membrane is also adapted to readily degrade over time. In this respect, it is desirable that the membrane is relatively thin, as specified above.

The cell bandage enables the direction of cells across the surface of a tissue as well as control of their distribution. While the cells are retained on the surface and/or in the framework of the biomaterial, their uniform distribution across the surface of the tissue is maintained. Accordingly, uniform development of the cells across the whole tissue surface is promoted. Where the bandage is used at the interface between two tissue surfaces, sandwiched between the tissues, to promote integration of the two tissues, continuous integration at the interface of the transplanted tissue and the surrounding tissue can be achieved. Density of the cells across the surface can be controlled by varying the loading of the cells onto the biomaterial.

The invention is not restricted to joining cartilage to cartilage. The same principle may be applied to the joining of other tissue surfaces such as cartilage to bone, bone to bone and ligament to bone. Cell type and biomaterial is selected appropriate to the tissues to be joined.

Preferred features of the various aspects of the invention are as to each other mutatis mutandis.

Embodiments of the invention will now be described purely by way of non-limiting example in which reference is made to the figures of which:

FIG. 1 shows the model system for testing the cell bandage. Panel a is a diagram showing the use of a cell bandage. The photograph in Panel b is an example of the model shortly after suturing. The photograph in Panel c is an example of the model after 8 weeks of culture.

FIG. 2 shows a no treatment control. In histological sections, no cells or extracellular matrix can be observed at the ring/core interface. Panel a is Van Gieson's staining at low magnification and Panel b is haematoxylin and eosin at higher magnification.

FIG. 3 shows a trypsin control. In histological sections some mild matrix formation at the interface between ring and core can be observed where the core and ring are in full contact. Panel a is Van Gieson's staining at low magnification; Panel b is Van Gieson's staining at higher magnification. In Panels c (low magnification) and d (higher magnification) fluorescence microscopy has be used to detect the natural autofluorescence of cartilage and this demonstrates only weak and patchy interstitial tissue at the interface.

FIG. 4 shows histology of a free cell coating control. Some areas of matrix formation can be observed in histological sections at the interface between ring and core, however, there was no apparent integration of the tissues. Panels a and b are Van Gieson's staining and Panel c is haematoxylin and eosin, all at higher magnification.

FIG. 5 shows cell labelling of free cell coating control. To assess the efficiency of coating, cells were labelled with a fluorescence dye (PKH26) before coating onto the cores. They were traced by fluorescence microscopy in frozen sections of the core-ring constructs 3 days after coating. Fluorescence microscopy indicates that the cores were not coated homogenously and efficiently. Some part of the core were coated with large clumps of cells (arrows) and most other parts without any cells. Panel a is low magnification and panel b is higher magnification.

FIG. 6 shows cell migration from a tissue engineered core. PGA scaffolds were seeded with chondrocytes, inserted in place of cores inside the rings and left to grow 6 weeks. Histological analysis shows evidence that cells implanted on the scaffold can degrade the adjacent ring of cartilage and migrate into the surrounding matrix (Panel a at low magnification, arrows indicate migrating cells; Panel b at higher magnification). In one experiment, cells were pre-labelled with a fluorescent dye before seeding onto PGA. In Panel c it can be seen that whilst the majority of these cells remain within the PGA, some are have clearly migrated into the ring cartilage (arrows).

FIG. 7 shows macroscopic appearance of a cell bandage after 8 weeks of culture. Controls with a cell-free bandage (PGA only) failed to integrate and there was an obvious gap between the core and ring in each case (Panel a). Cores reinserted using a cell bandage generated an interstitial tissue that completely filled the interface producing clear gross tissue continuity across the core and the ring (Panel b). In one experiment, two separate core/ring constructs were grown together using a cell bandage between them, demonstrating a tight integration of the tissues (Panels c and d).

FIG. 8 shows microscopic appearance of a cell bandage after 8 weeks of culture. Cores reinserted using a cell bandage generated an interstitial tissue that completely filled the interface producing effective integration across the core and the ring. Representative examples of histological sections stained with haematoxylin and eosin are shown at higher magnification in Panels a and b. In Panel a there is evidence that cells from the bandage migrated into the core and ring tissues themselves (arrows).

FIG. 9 is a diagram showing the hyaline or meniscal cartilage cell bandage sandwich model.

FIG. 10 shows the macroscopic appearance of the hyaline cartilage sandwich model after 40 days in culture. Two separate sandwich constructs can be seen within the same Petri dish. One of these has been labelled to indicate the location of the cell bandage in relation to the two pieces of hyaline cartilage.

FIG. 11 shows the influence of collagen membrane surface roughness on cartilage-integration. Bovine nasal chondrocytes seeded onto a 1 mm collagen membrane were placed between two pieces of nasal septum hyaline cartilage and cultured for 40 days. Histological analysis at low power (×10, panel A) shows a clear difference between the rough and smooth surfaces in the way they have interacted with the adjacent cartilage. At higher power (×20) the smooth surface can be seen to have a clear demarcating border with the cartilage, indicating poor integration (panel B), although cell migration is clearly on-going. However the rough surface has no clear border with the adjacent cartilage, indicating effective integration (panel C).

FIG. 12 shows the influence of collagen membrane thickness on cartilage integration. Bovine nasal chondrocytes seeded onto 1 mm (thick) or 0.5 mm (thin) collagen membranes were each placed between two pieces of nasal septum hyaline cartilage and cultured for 20 days. Histological analysis shows no evidence of integration at this time point with the thick membrane but effective integration at the rough surface of the thin membrane.

FIG. 16 shows effective meniscal cartilage integration in the whole meniscus organ culture model after 45 days in culture. Note the similarity of the interface tissue with surrounding meniscal tissue.

Example 1

Figure 1:
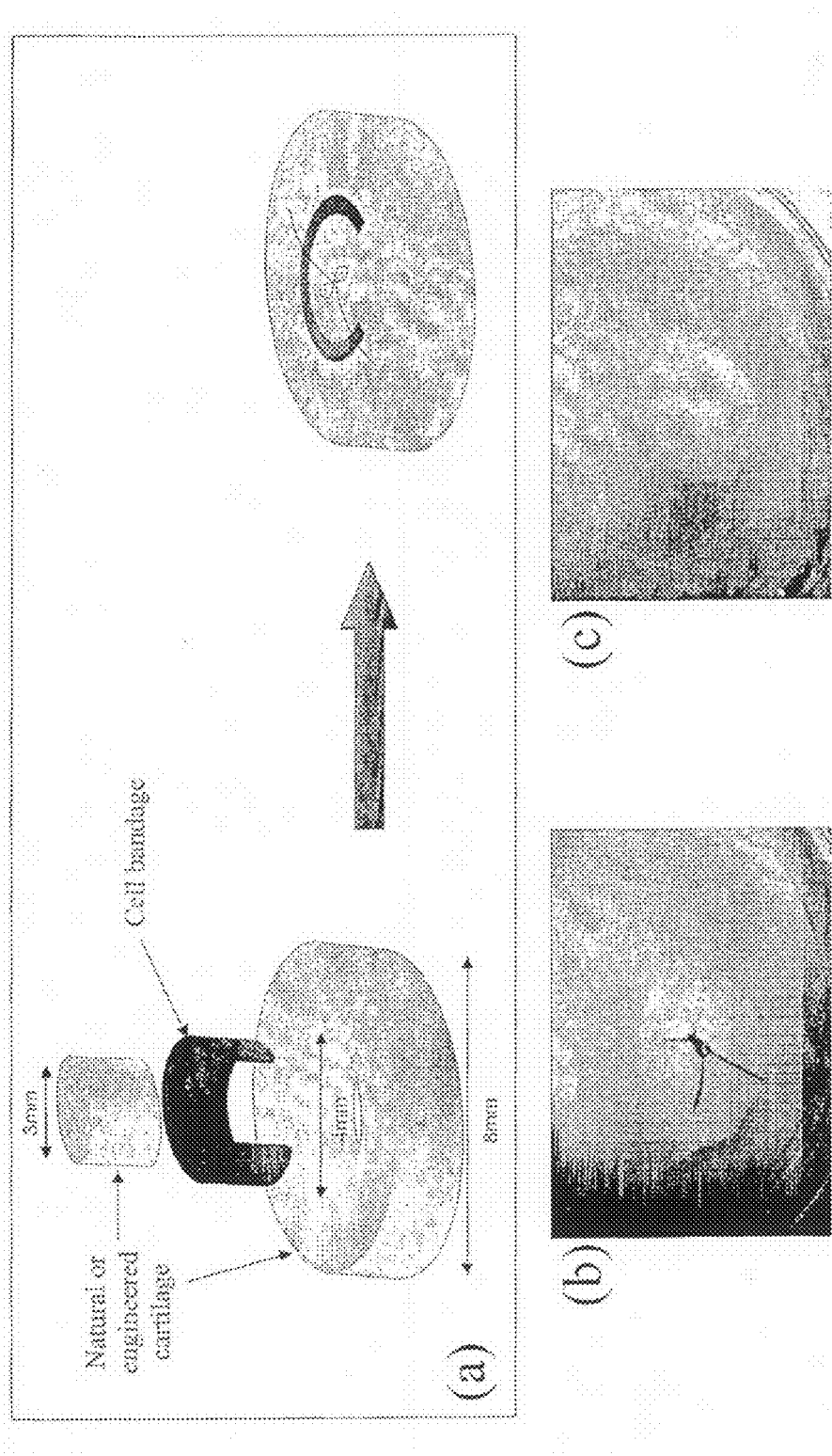

Methods
Cartilage Explants

Natural Cartilage plugs (8 mm in diameter) were harvested from adult bovine nasal cartilage using a dermal biopsy punch (Schuco International London Ltd). The disks were 8 mm diameter×4 mm thickness, obtained from the middle of nasal septum. They were rinsed with phosphate buffered saline (PBS) and incubated in PBS supplemented with 10× Penicillin/Streptomycin and Fungizone for 20 minutes. The disks were kept in DMEM medium containing 10% FCS (Complete Medium) for later experiments. Dermal punches were also used to make 3 mm (or 4 mm whenever cell bandage was used) diameter cores inside the 8 mm disks. The remaining cartilage was used to make monolayer chondrocytes.

Experimental Design

The model used in this study is the core in a ring cartilage assembly (FIG. 1) (Obradovic et al., 2001). The cores were press-fit into the rings and sutured together using #4-0 silk and cutting FS-3 needles. One or two stitches were applied as distant as possible from the core-ring interface. A series of controls were used for comparison with the cell bandage. In the first control (n=10), the core and the ring were assembled without any cell coating or filling at the interface. In the second control, core and rings were treated with Trypsin (0.25% w/v; Sigma) before assembly. In the third control, cores were coated with matrix-free chondrocytes. They were enzymatically isolated from residual cartilage (Kafienah et al., 2002) following core and ring preparation. The cells were expanded in Complete Medium containing FGF-2 (10 ng/ml) to increase their number and inhibit their dedifferentiation in culture (Martin et al., 1999). On coating day, expanding chondrocytes were trypsinized, counted and suspended at 500,000 cells/ml in complete medium. Inner cores were incubated in the cell suspension in 6 well plates coated with a thin layer of 1% agarose gel. The plates were incubated on a gently rotating platform for 24 hours. In some instances, the core was pre-treated with trypsin (0.25% w/v for 20 min) to remove proteoglycans that may hinder cell attachment (Hunziker et al., 1998). In the fourth control, immature tissue engineered cartilage was used as cores. Polyglycolic acid (PGA) scaffolds (4 mm wide×2 mm thick disks) were seeded with chondrocytes according to our established methods (Kafienah et al., 2003; Kafienah et al., 2002). The cell-scaffold construct was inserted in the ring hole and sutured as above.

The invention of the cell bandage is exemplified using a PGA scaffold in between the core and the ring. PGA scaffolds (1 cm wide×2 mm thick) were seeded with cells as previously described (Kafienah et al., 2002). The cell-scaffold construct was sandwiched between the core and the ring straight after seeding and the whole assembly was sutured as described above. Unseeded scaffolds were used as controls.

In all cases, assembled explants were cultured in expansion complete medium with FGF-2 for 4 days followed by differentiation medium consisting of complete medium with insulin (10 mg/mL; Sigma) and ascorbic acid (50 mg/mL; Sigma). The medium was replenished every 2-3 days.

Cell Labelling

To assess the efficiency of coating and trace cell migration, chondrocytes were labelled with the fluorescent dye PKH26 (Sigma). The labelling procedure was performed according to the manufacturer's protocol with some modifications. Briefly, after trypsin release, $10 \times 10^6$ cells were washed once in calcium and magnesium free PBS and resuspended into 500 µl of buffer C provided by the manufacturer in the labelling kit. The cell suspension were mixed with 500 µl of the labelling solution containing PKH26 in a dilution buffer to the optimised final concentration. Labelling was allowed for 8 minutes at 25° C. The reaction was stopped by adding 1 mL FBS. The pellets were transferred to new tubes and washed four times in complete medium. Cell viability was assessed by trypan blue and was almost 100%.

Histological and Immunohistochemical Analyses

At 4 weeks or 8 weeks the explants were fixed in 10% neutral buffered formalin and embedded in paraffin and sectioned (8 µm thick). Sections were stained with Safranin-O for proteoglycans, H&E for morphology or Van Gieson for collagen according to standard protocols. Explants coated with fluorescence labelled cells were frozen immediately (at 4 or 8 weeks) on dry ice and the tissue stored at −70° C. prior to sectioning. For explants that were coated with fluorescence-labeled cells, frozen tissues were mounted using O.C.T. compound. Sections at 8 µm were prepared using cryo-section. Slides were air dried for at least 1 hour at room temperature and mounted using 1-2 drops cyanoacrylate.

Image Acquisition and Analysis

Digital images were acquired using Spot camera and Spot software version 3.0.4 (Diagnostic Instruments Sterling Heights, Mich.).

Results

The controls used for comparison with the cell bandage are summarised below:
1. No treatment control (core reinserted with no cell bandage)
2. Trypsin control (no cell bandage; core and ring pre-treated with 0.25% w/v trypsin instead of cell bandage as an alternative mechanism of integration described elsewhere)
3. Free cell coating control (no cell bandage; core pre-incubated for 24 hours with chondrocytes suspended in culture medium at 500,000/ml to coat the cartilage surface with free cells)
4. Tissue engineered core (cartilage engineered on a disc of PGA inserted into the ring instead of a cartilage core)

No Treatment Control

Figure 2:
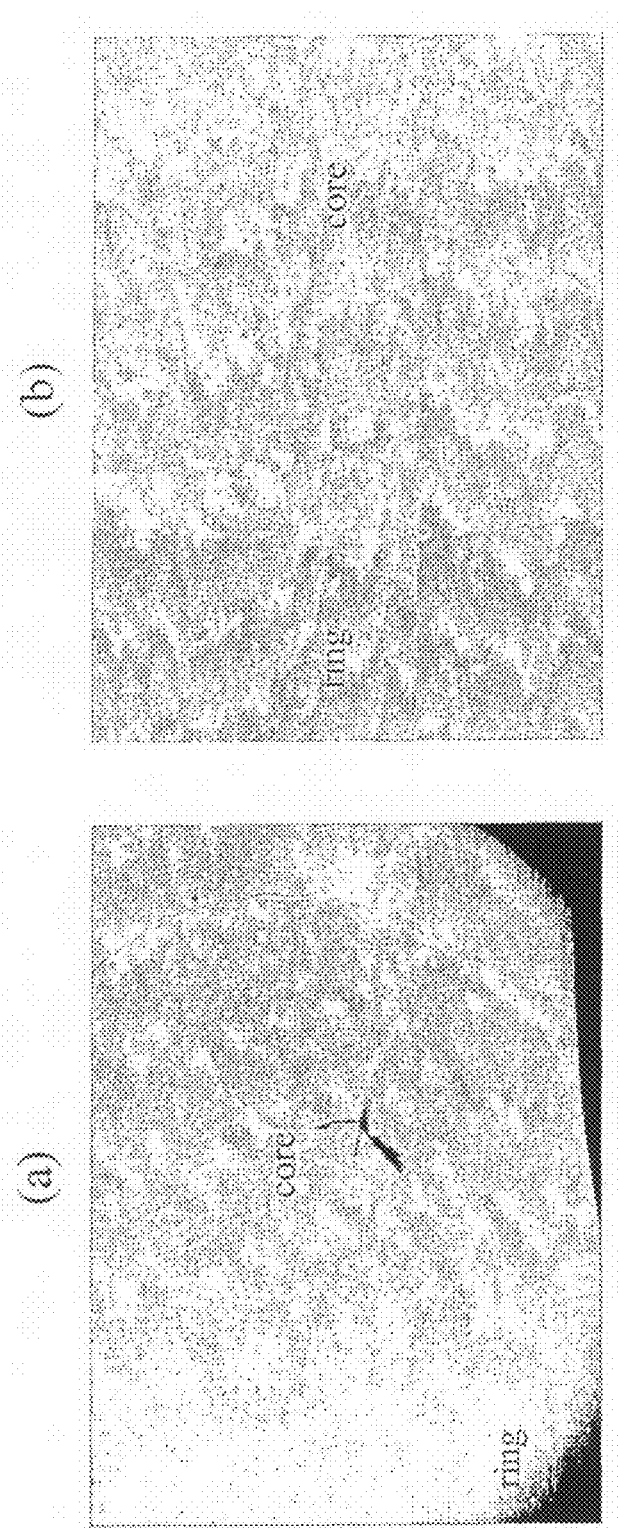

Cores reinserted with no cells, bandage or trypsin treatment cannot integrate with the surrounding cartilage. The histological sections in FIG. 2 show no evidence of interaction between the cartilage pieces with clear space at the interface.

Trypsin Control

Figure 3:
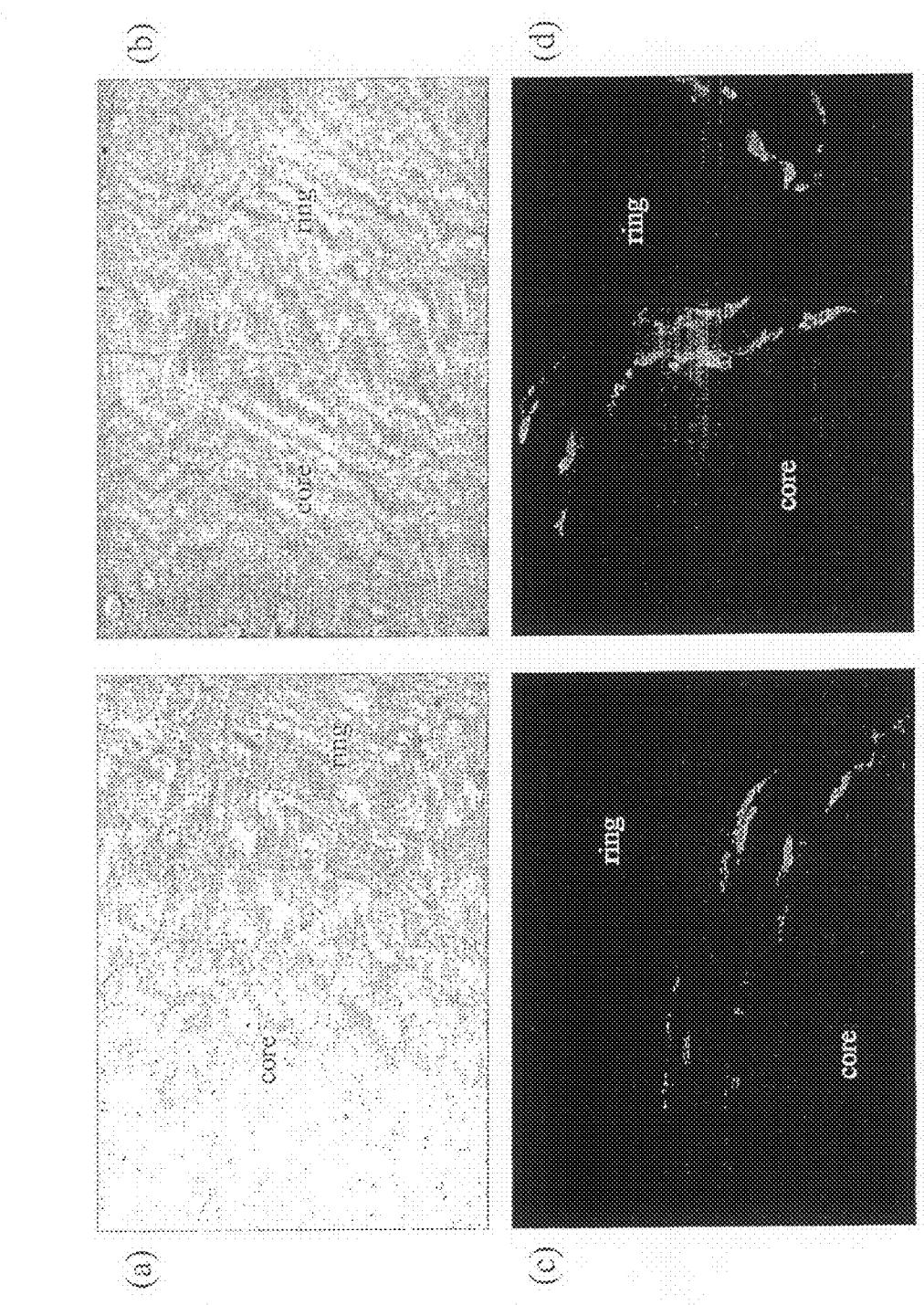

Cores treated with trypsin and then reinserted showed a mild capacity to integrate with the ring tissue. There was some formation of an interstitial matrix where the core and ring were in full contact, however the accumulation of matrix was not extensive even after 8 weeks of culture (FIG. 3).

Free Cell Coating Control

Figure 4:
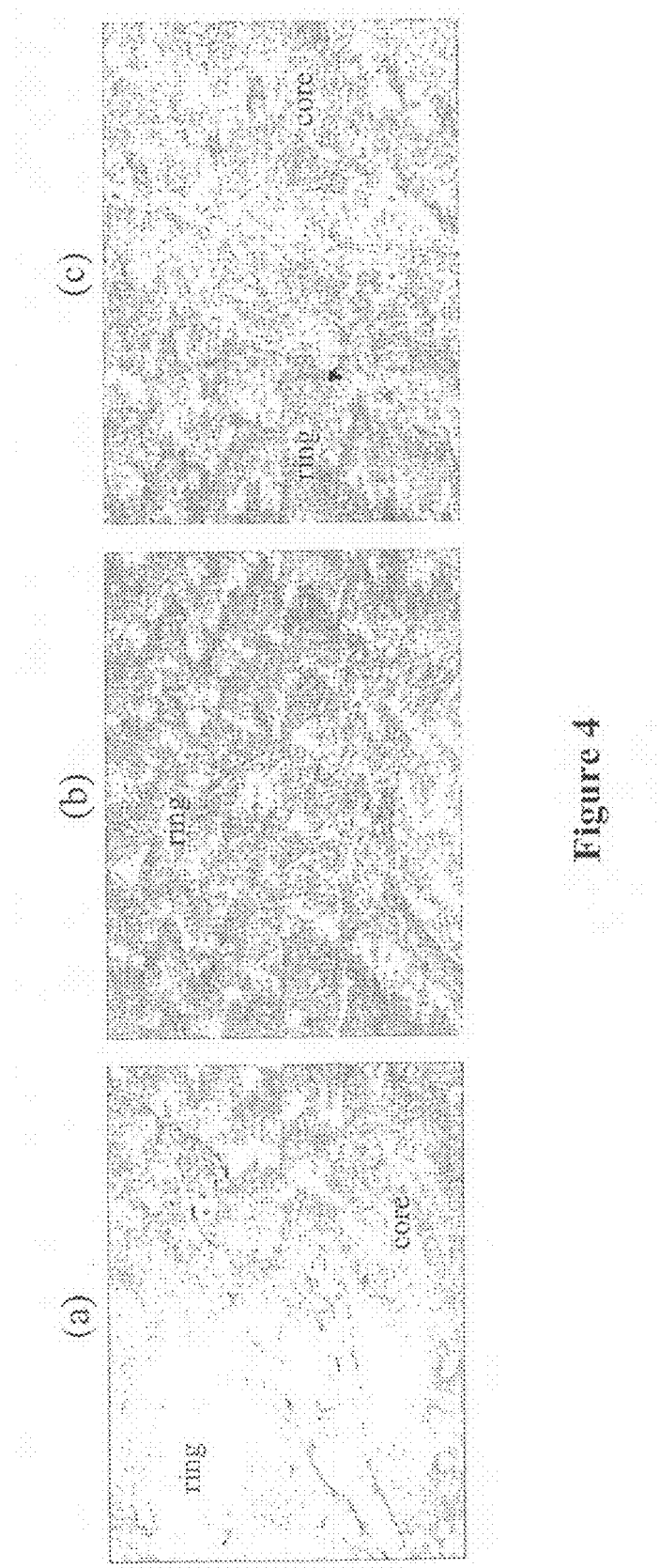
Figure 5:
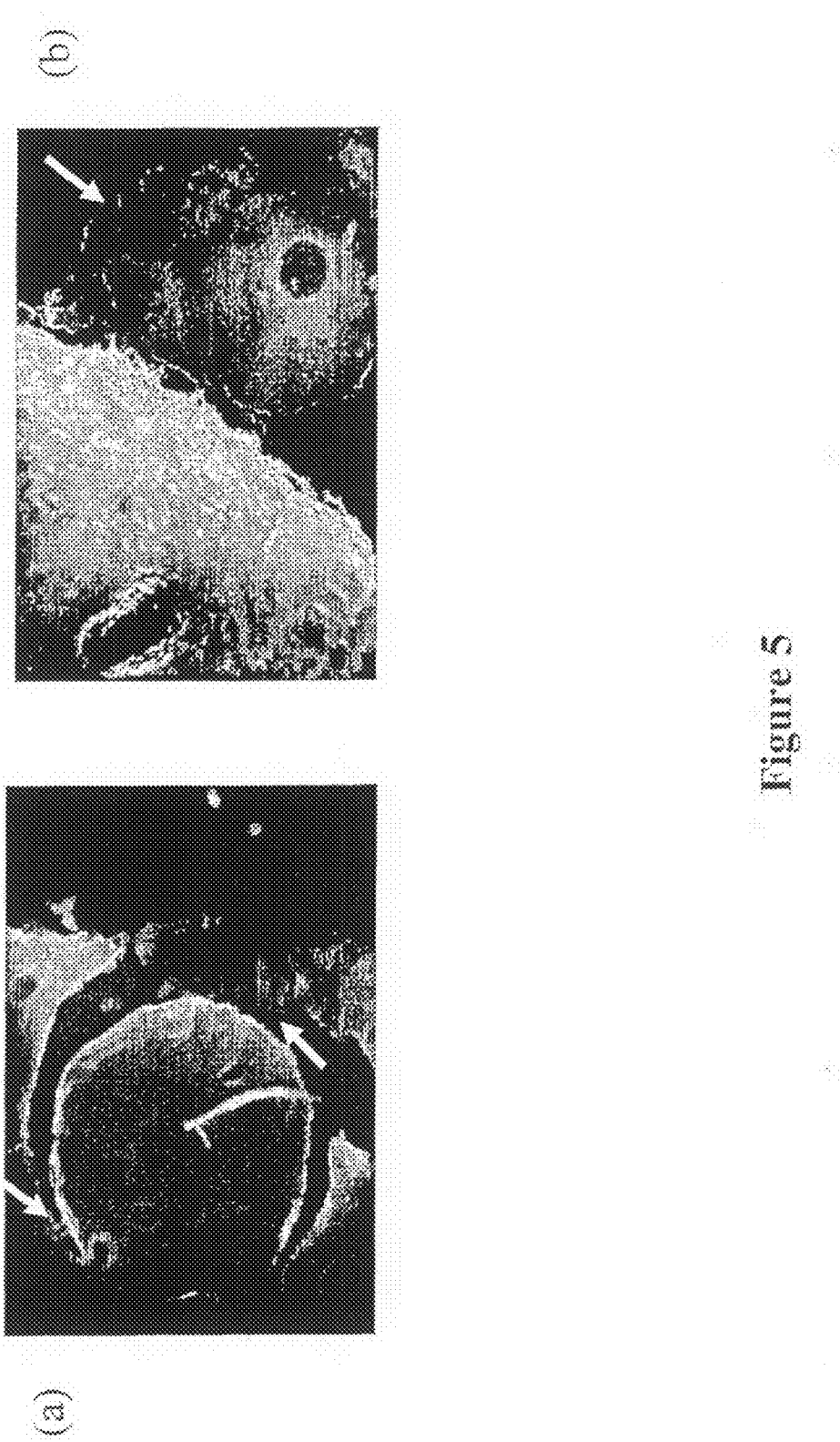

Cores pre-incubated with chondrocytes and then reinserted showed evidence of some matrix formation at localized patches around the tissue, although there was no evidence of integration of the ring and core (FIG. 4). The reason for this was identified by pre-labelling the coating cells with a fluorescent dye. In this way it is apparent that the coating cells migrate onto the core tissue in discreet clumps, creating focal areas where interaction with the ring tissue may occur, but not allowing effective tissue integration (FIG. 5). This demonstrates that in order to achieve integration a method to coat cells more evenly around the cartilage surface is required which allows close interaction between these cells and the surrounding cartilage.

Tissue Engineered Core

Figure 6:
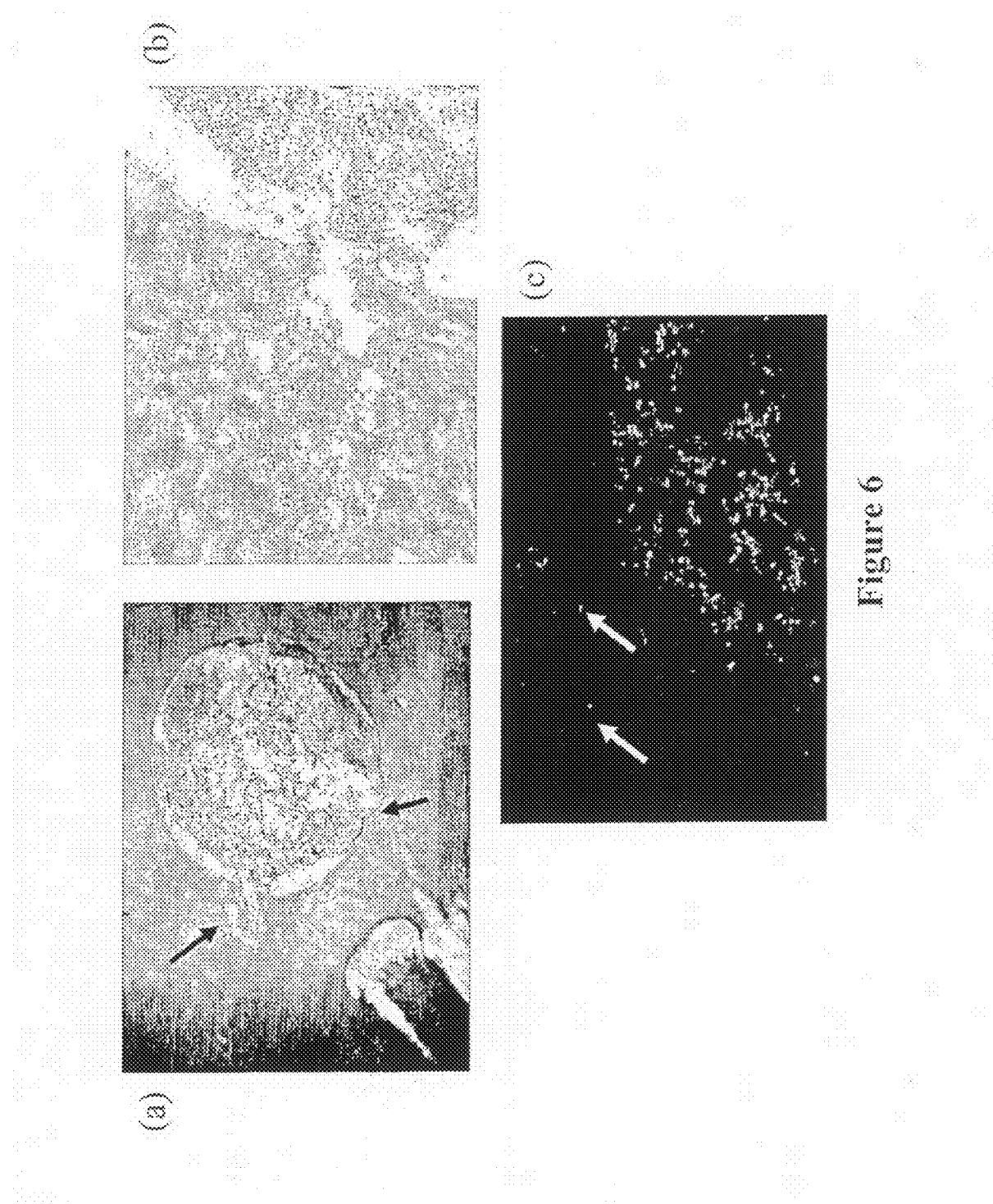

The present invention solves the problem of how to deliver cells to the cartilage surface by using a biomaterial scaffold that will allow seeded cells to migrate into the tissue. As a proof of principle, a tissue engineered core was created by seeding chondrocytes onto PGA and this was implanted into the ring instead of the original cartilage core. In this way clear evidence of chondrocytes degrading the surrounding cartilage matrix and migrating into it was observed (FIG. 6). The inventors' hypothesis is that these migrating cells will synthesise new cartilage to fill the space through which they have migrated.

Cell Bandage

Figure 7:
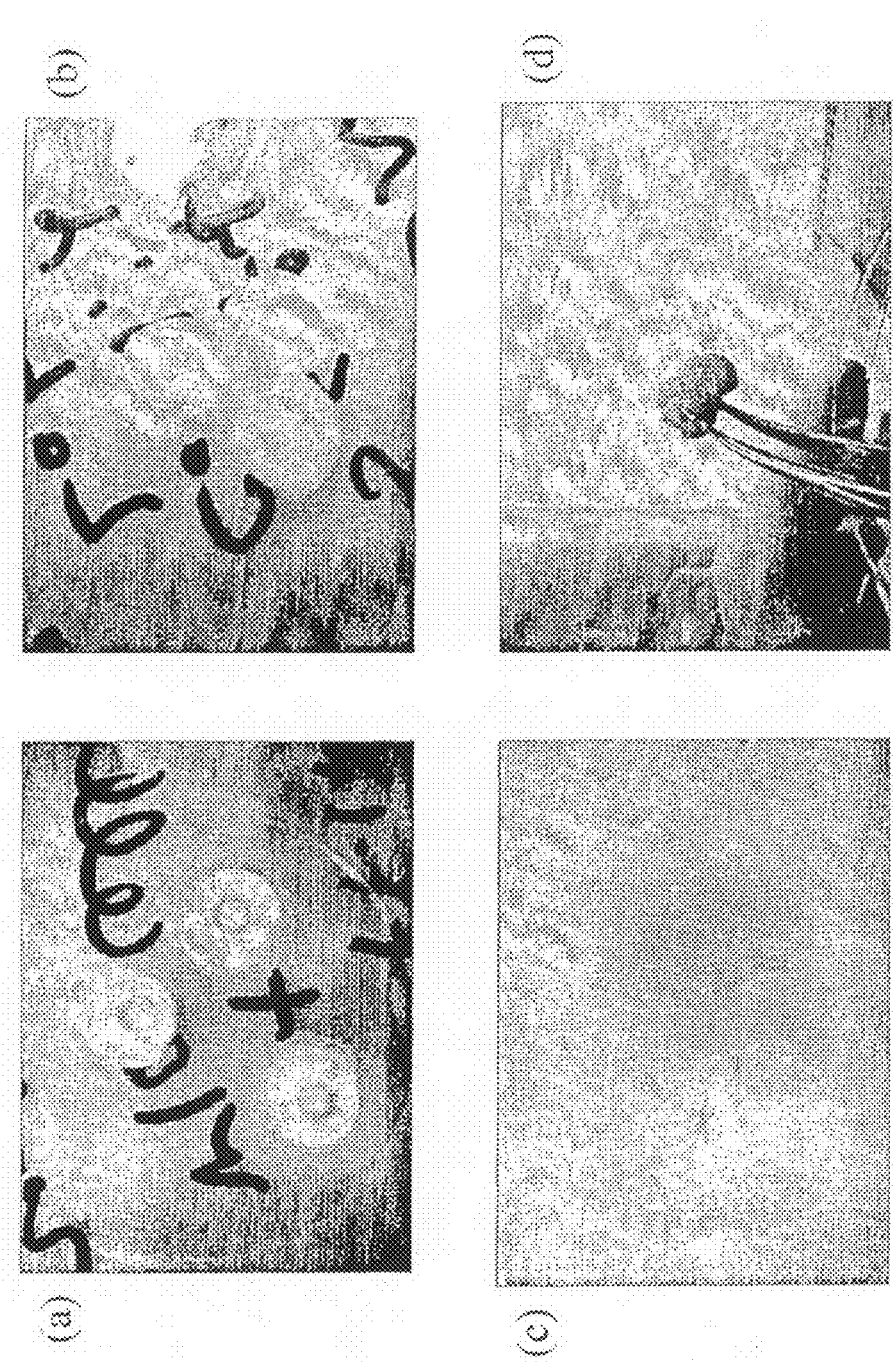
Figure 8:
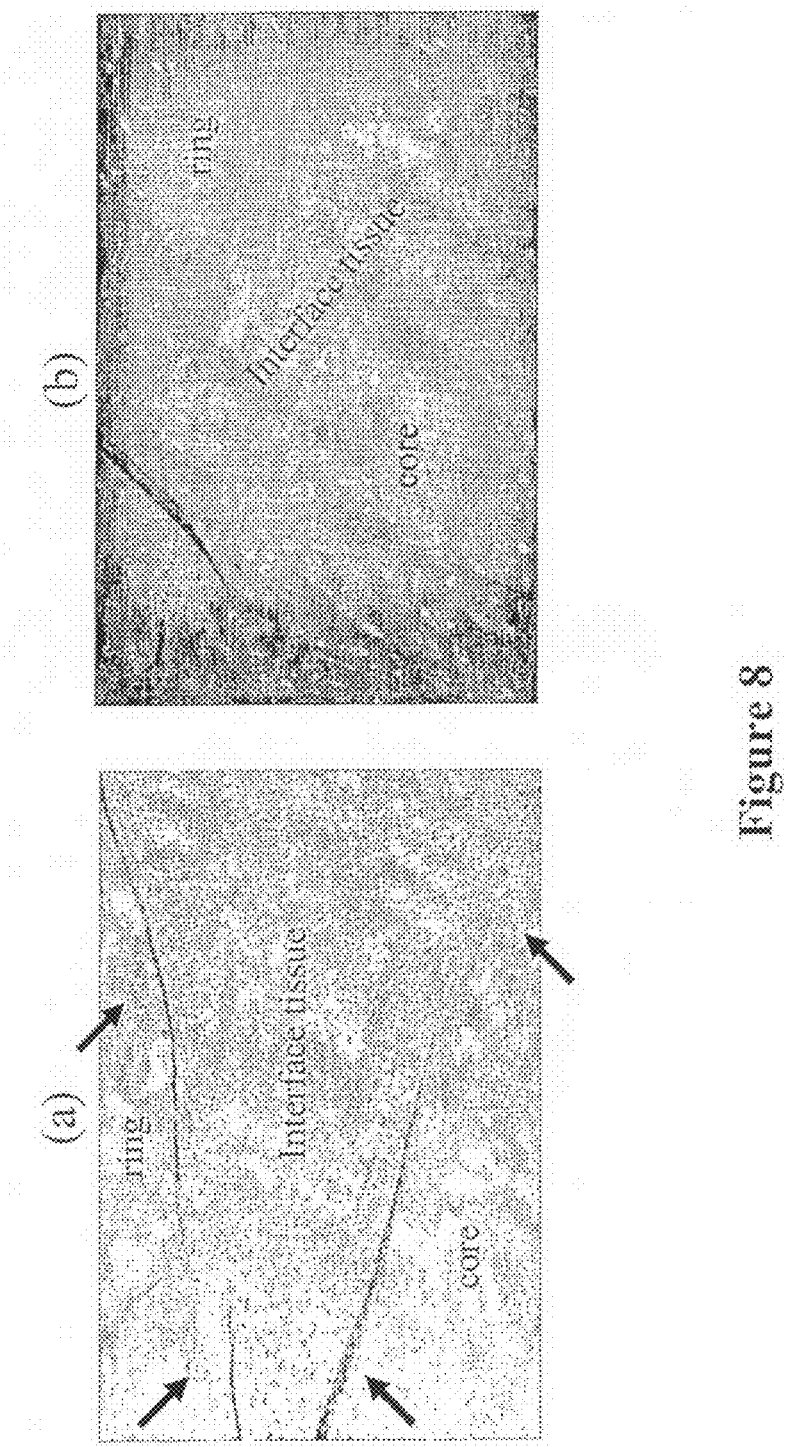

The final test of the invention was to use the cell bandage sandwiched between two pieces of cartilage, as described in FIG. 1. In control experiments using PGA without cells there was no cartilage integration (FIG. 7a), however in cultures with the cell bandage there was very clear evidence of good cartilage integration both macroscopically (FIG. 7) and microscopically (FIG. 8).

Example 2

Figure 9:
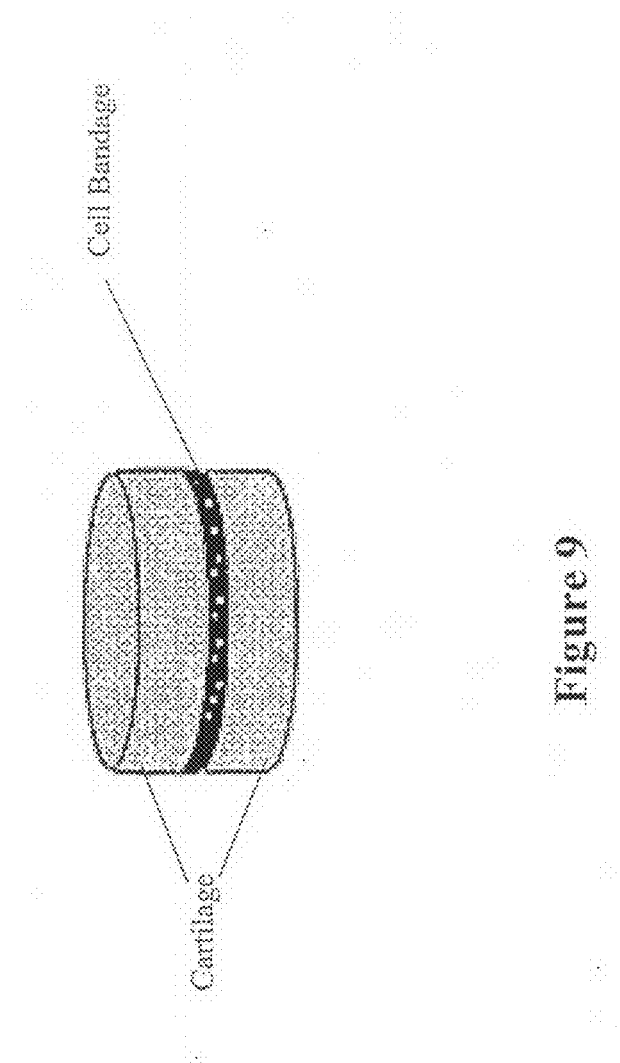
Figure 10:
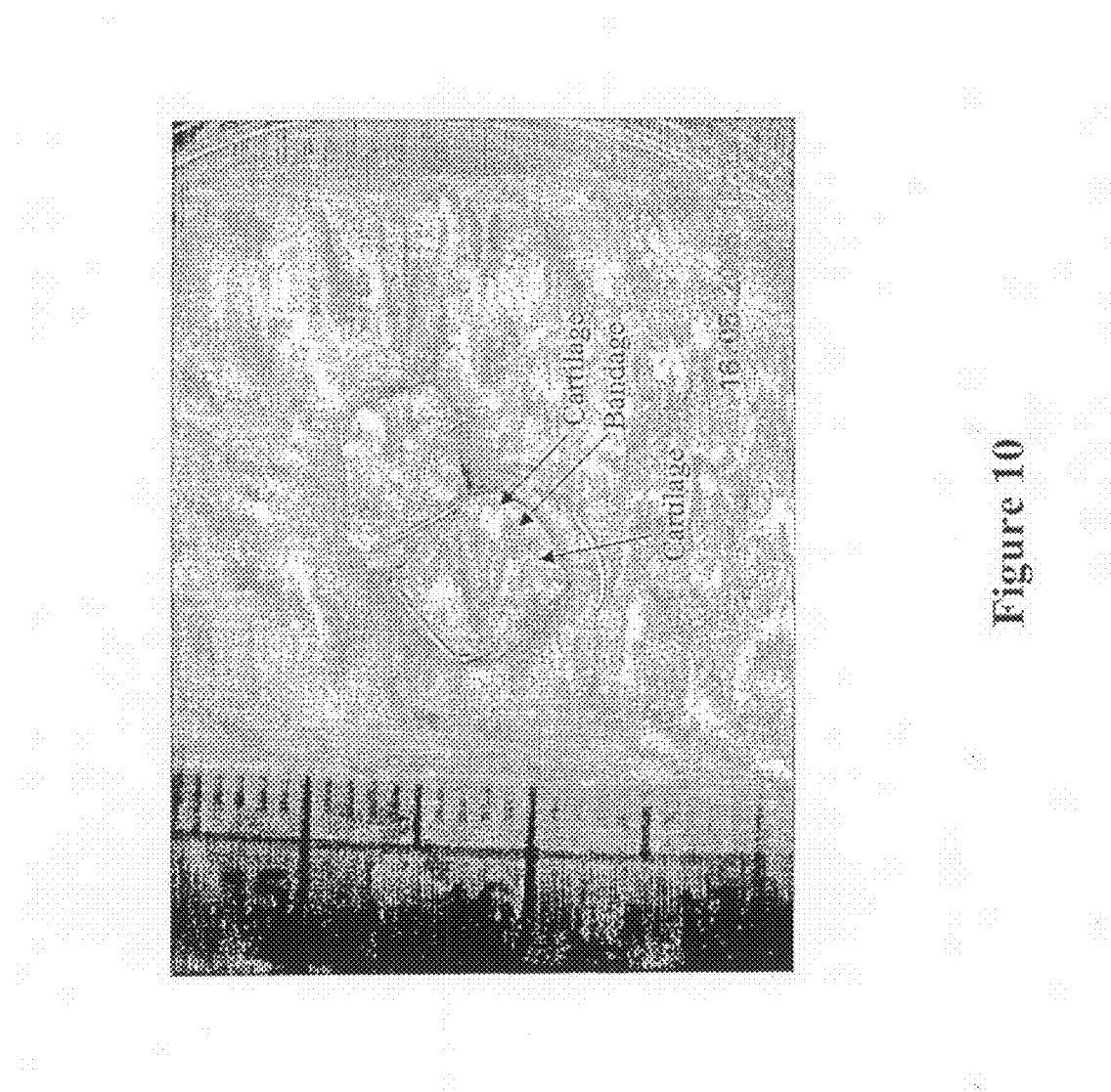

Determining the Parameters of the Scaffold Best Suited to Closing Space Rather than Filling Space Method We used the sandwich model for cartilage integration in which 2 pieces of bovine nasal septum hyaline cartilage are placed together with a cell bandage in between them (FIG. 9). For this set of experiments the bandage consisted of a bovine nasal chondrocytes seeded onto a thick (1 mm) or thin (0.5 mm) collagen membrane obtained from "Geistlich". These membranes each have a "rough" surface and a "smooth" surface. The sandwich was held together using a staple-clip (FIG. 10). By 40 days of culture there was macroscopic evidence for integration (FIG. 10).

Results

Surface Roughness and Integration

Figure 11:
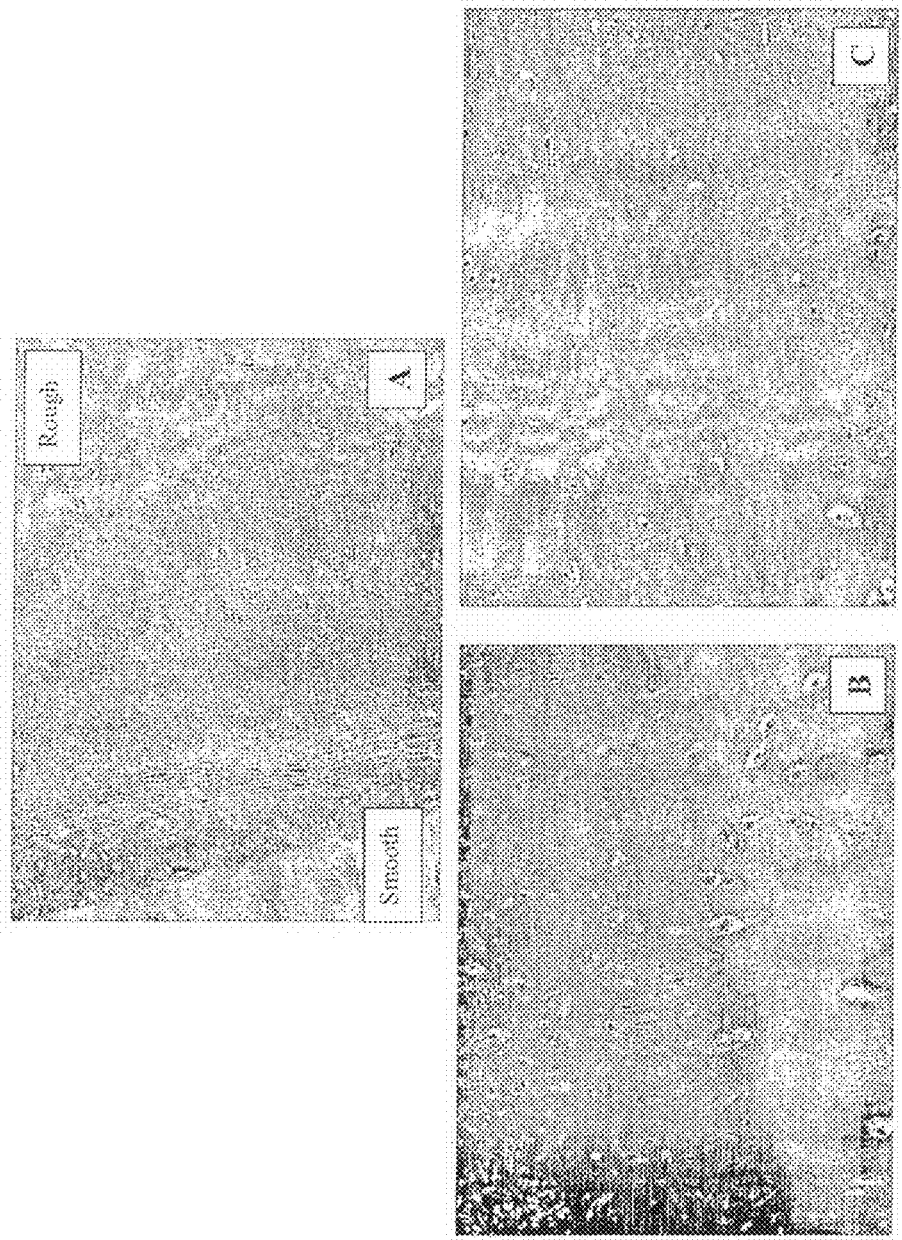

We tested the hypothesis that a rough surface would enhance integration by encouraging a more rapid migration of cells out of the scaffold into the surrounding tissue. By 40 days of culture, at the histological level there was clear evidence of integration at the interface of the rough surface of the collagen membrane with the hyaline cartilage whereas the smooth surface showed little evidence of integration, using a thick membrane (FIG. 11). However there was also evidence of cell migration from the smooth surface which would be expected to result in integration after a longer culture time. These findings suggest that by 40 days the chondrocytes had migrated out of the rough surface and promoted tissue integration whereas at the smooth surface the cell migration was still on-going ahead of effective integration.

Membrane Thickness and Integration

Figure 12:
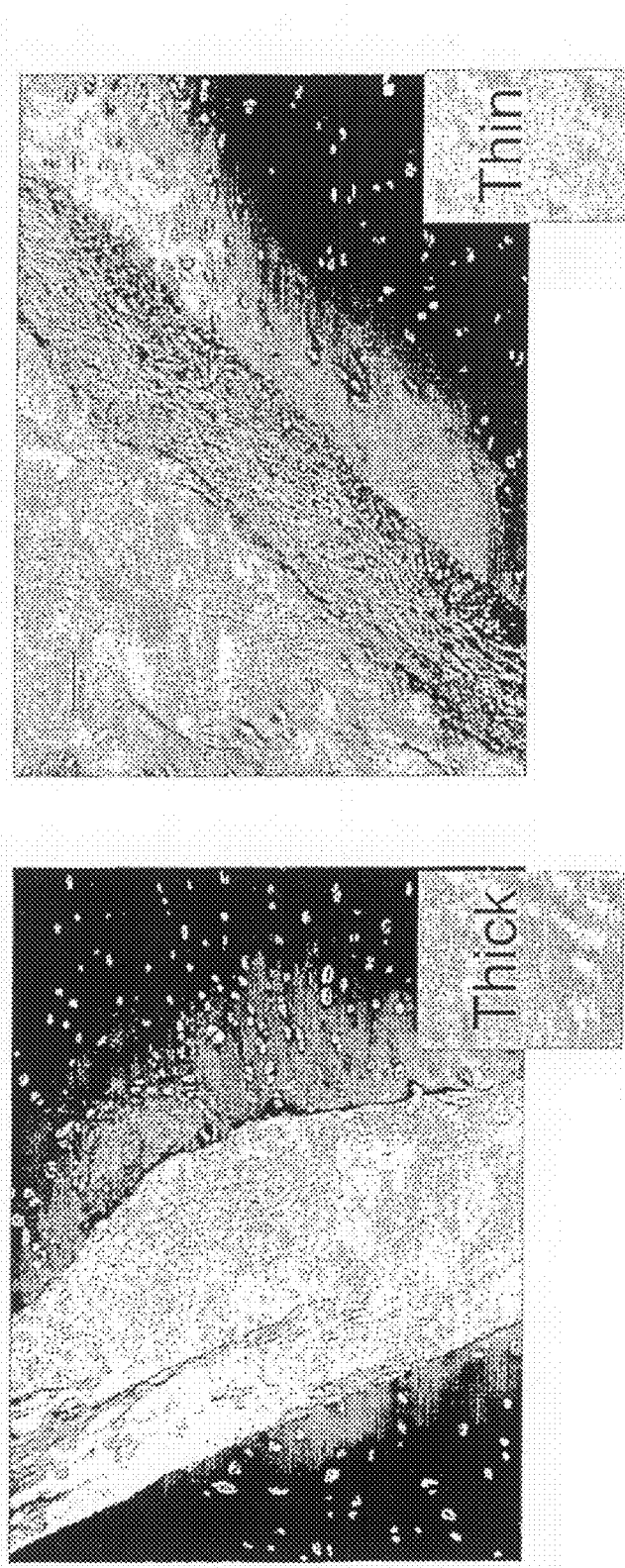

We tested the hypothesis that thin scaffolds would occupy less space and so encourage more rapid integration than thick scaffolds. After 20 days of culture the thick scaffold showed no evidence of cartilage integration whereas the thin scaffold was already inducing effective integration at the rough surface (FIG. 12). These findings confirm that thin scaffolds are most effective when integration (removal of space) is the aim.

Example 3

Determining the Best Cell Types for Repairing Hyaline and Meniscal Cartilage

Methods

Figure 13:
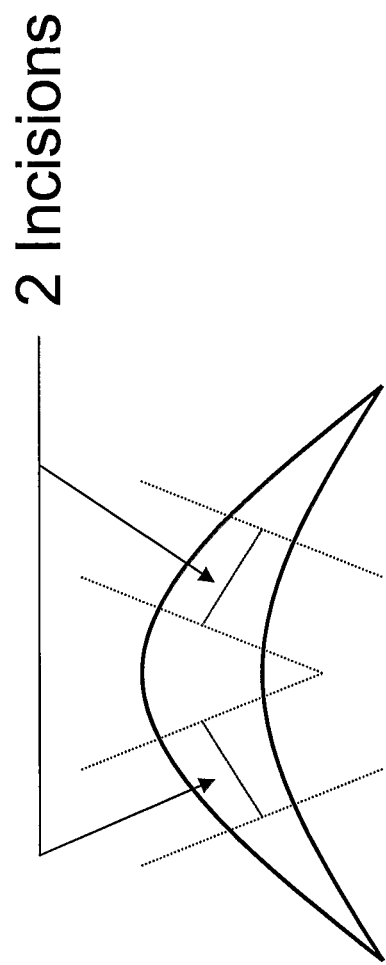
FIG. 13 is a diagram showing the whole meniscus organ culture model
Figure 14:
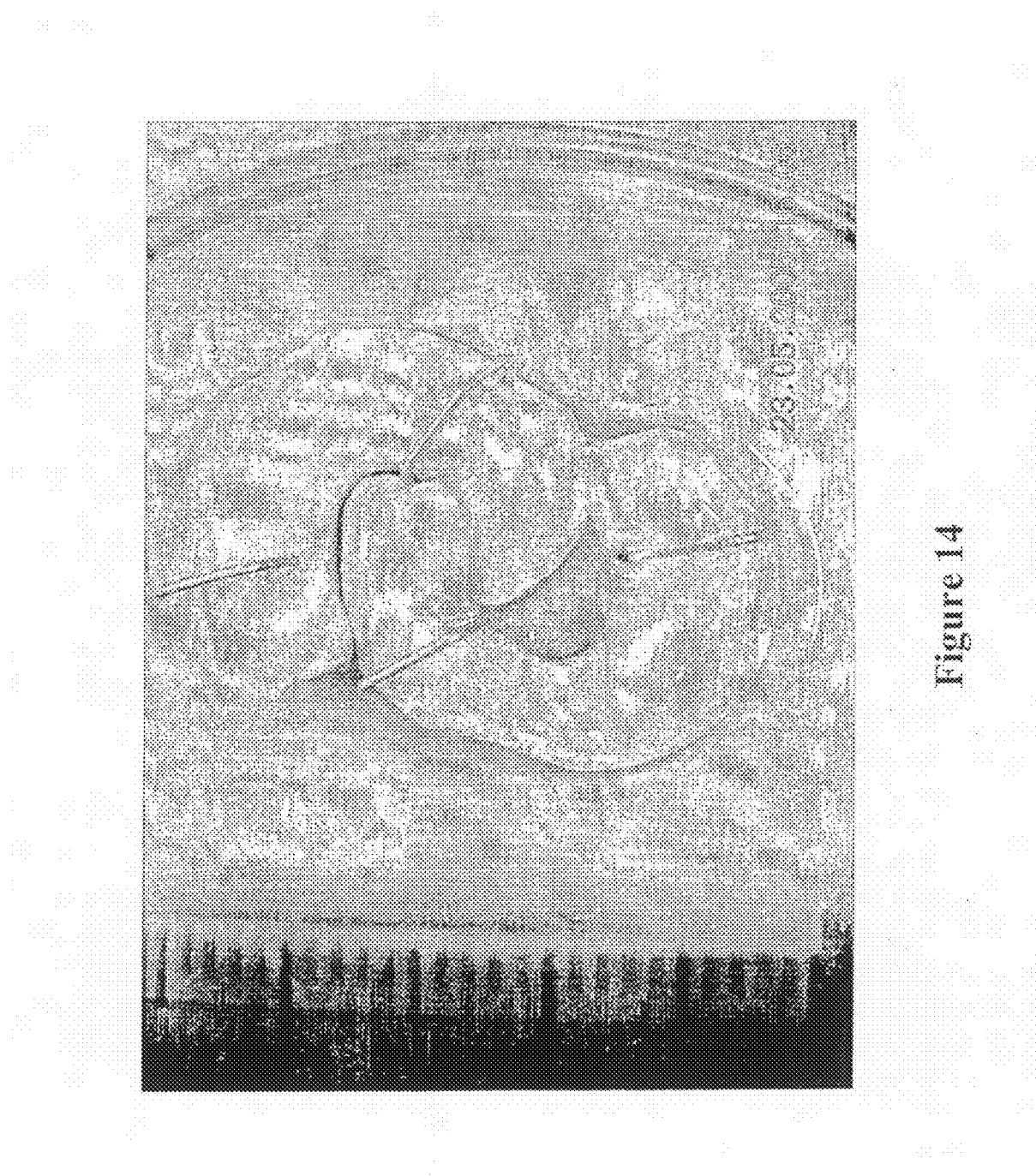
FIG. 14 shows the macroscopic appearance of the meniscal cartilage whole organ model after 45 days in culture.

We used the sandwich model for cartilage integration shown in FIGS. 9 and 10 using either bovine hyaline cartilage or ovine meniscal cartilage. In each case we compared the use of bovine/ovine articular cartilage chondrocytes, ovine meniscal fibrochondrocytes chondrocytes, bovine nasal chondrocytes or human bone marrow mesenchymal stem cells. We also used a whole-organ model of meniscal cartilage repair. Two incisions were made in whole menisci and a cell bandage was inserted into each one (FIG. 13). Staple clips were used to hold the bandage in place (FIG. 14).

Results

Cell Type in Cartilage Sandwich Model

Figure 15:
FIG. 15 shows effective meniscal cartilage integration in the sandwich model using a cell bandage made from stem cells, after 40 days of culture. Note the lack of any clear demarcating border, indicating excellent integration.

In both hyaline and meniscal cartilage sandwich systems, best results were obtained using either nasal chondrocytes or stem cells. Articular and meniscal chondrocytes were always inferior. However for meniscal cartilage repair the stem cells appeared to produce a particularly effective integration (FIG. 15). Therefore nasal or stem cells are the cells of preference hyaline or meniscal cartilage integration.

Cell Type in Whole Meniscus Model

Stem cells produced a superior integration compared with all other cell types, with the production of an interface tissue that closely resembled the surrounding meniscal tissue (FIG. 16). Therefore stem cells are the cell of preference for meniscal cartilage integration.

REFERENCES

AHSAN, T. & SAH, R. L. (1999). Biomechanics of integrative cartilage repair. *Osteoarthritis Cartilage*, 7, 29-40.

BUCKWALTER, J. A. & MANKIN, H. J. (1998). Articular cartilage repair and transplantation. *Arthritis Rheum*, 41, 1331-42.

DONOHUE, J. M., BUSS, D., OEGEMA, T. R., JR. & THOMPSON, R. C., JR. (1983). The effects of indirect blunt trauma on adult canine articular cartilage. *J Bone Joint Surg Am*, 65, 948-57.

GILBERT, J. E. (1998). Current treatment options for the restoration of articular cartilage. *Am J Knee Surg*, 11, 42-6.

GILLOGLY, S. D. (2003). Treatment of large full-thickness chondral defects of the knee with autologous chondrocyte implantation. *Arthroscopy*, 19 Suppl 1, 147-53.

HUNZIKER, E. B. & KAPFINGER, E. (1998). Removal of proteoglycans from the surface of defects in articular cartilage transiently enhances coverage by repair cells. *J Bone Joint Surg Br*, 80, 144-50. HUNZIKER, E. B. (1999). Articular cartilage repair: are the intrinsic biological constraints undermining this process insuperable? *Osteoarthritis Cartilage*, 7, 15-28.

HUNZIKER, E. B. (1999). Articular cartilage repair: are the intrinsic biological constraints undermining this process insuperable? *Osteoarthritis Cartilage,* 7, 15-28.

HUNZIKER, E. B. (2002). Articular cartilage repair: basic science and clinical progress. A review of the current status and prospects. *Osteoarthritis Cartilage,* 10, 432-63.

KAFIENAH, W., AL-FAYEZ, F., HOLLANDER, A. P. & BARKER, M. D. (2003). Inhibition of cartilage degradation: a combined tissue engineering and gene therapy approach. *Arthritis Rheum,* 48, 709-18.

KAFIENAH, W., JAKOB, M., DEMARTEAU, O., FRAZER, A., BARKER, M. D., MARTIN, I. & HOLLANDER, A. P. (2002). Three-dimensional tissue engineering of hyaline cartilage: comparison of adult nasal and articular chondrocytes. *Tissue Eng,* 8, 817-26.

MARTIN, I., VUNJAK-NOVAKOVIC, G., YANG, J., LANGER, R. & FREED, L. E. (1999). Mammalian chondrocytes expanded in the presence of fibroblast growth factor 2 maintain the ability to differentiate and regenerate three-dimensional cartilaginous tissue. *Exp Cell Res,* 253, 681-8.

OBRADOVIC, B., MARTIN, I., PADERA, R. F., TREPPO, S., FREED, L. E. & VUNJAK-NOVAKOVIC, G. (2001). Integration of engineered cartilage. *J Orthop Res,* 19, 1089-97.

PERETTI, G. M., BONASSAR, L. J., CARUSO, E. M., RANDOLPH, M. A., TRAHAN, C. A. & ZALESKE, D. J. (1999). Biomechanical analysis of a chondrocyte-based repair model of articular cartilage. *Tissue Eng,* 5, 317-26.

PERETTI, G. M., ZAPOROJAN, V., SPANGENBERG, K. M., RANDOLPH, M. A., FELLERS, J. & BONASSAR, L. J. (2003). Cell-based bonding of articular cartilage: An extended study. *J Biomed Mater Res,* 64A, 517-24.

REDMAN, S. N., DOWTHWAITE, G. P., THOMSON, B. M. & ARCHER, C. W. (2004). The cellular responses of articular cartilage to sharp and blunt trauma. *Osteoarthritis Cartilage,* 12, 106-16.

REINDEL, E. S., AYROSO, A. M., CHEN, A. C., CHUN, D. M., SCHINAGL, R. M. & SAH, R. L. (1995). Integrative repair of articular cartilage in vitro: adhesive strength of the interface region. *J Orthop Res,* 13, 751-60.

SCHINAGL, R. M., KURTIS, M. S., ELLIS, K. D., CHIEN, S. & SAH, R. L. (1999). Effect of seeding duration on the strength of chondrocyte adhesion to articular cartilage. *J Orthop Res,* 17, 121-9.

SHAPIRO, F., KOIDE, S. & GLIMCHER, M. J. (1993). Cell origin and differentiation in the repair of full-thickness defects of articular cartilage. *J Bone Joint Surg Am,* 75, 532-53.

THOMPSON, R. C., JR., OEGEMA, T. R., JR., LEWIS, J. L. & WALLACE, L. (1991). Osteoarthrotic changes after acute transarticular load. An animal model. *J Bone Joint Surg Am,* 73, 990-1001.

The invention claimed is:

1. A cell bandage comprising
a sheet of biomaterial, wherein said biomaterial has cells distributed on and within it, said sheet has cells at or on both surfaces, and the biomaterial is rough on both of said surfaces and has an open structure at both said surfaces, thereby promoting release of said cells from each surface of the bandage following surgical implantation and promoting migration of cells from each surface of the bandage following a surgical implantation, wherein said cell bandage is less than 1.0 mm thick, and is for applying cells in close apposition to the surface of a tissue, and said biomaterial is biodegradable in vivo.

2. The cell bandage according to claim 1, wherein the cells are cartilage producing cells or cells capable of producing cartilage.

3. The cell bandage according to claim 1, wherein the biomaterial is synthetic.

4. The cell bandage according to claim 1, wherein the biomaterial is naturally derived.

5. The cell bandage according to claim 1, wherein said cell bandage promotes integration of transplanted or implanted cartilage and bone at the site of surgical implantation.

6. The cell bandage according to claim 1, wherein said cell bandage repairs a meniscal tear.

7. The cell bandage according to claim 1, wherein said cell bandage promotes integration of two or more pieces of engineered cartilage.

8. The cell bandage according to claim 1, wherein the cells are evenly distributed throughout the volume of the cell bandage, or over the entire surface of each side of the cell bandage.

9. A tissue sandwich comprising:
a first tissue;
a cell bandage according to claim 1; and
a second tissue, wherein the cell bandage is sandwiched between the first tissue and the second tissue, thereby integrating the first tissue with the second tissue.

10. A method for delivering cells across opposing tissue surfaces, the method comprising providing a cell bandage according to claim 1 at the interface between the surfaces, wherein, after application of the cell bandage, cells are released from the cell bandage to each tissue.

11. The method according to claim 10, wherein the tissue is cartilaginous and the cells are cartilage producing cells or cells capable of producing cartilage.

12. A method for bonding two or more tissues, the method comprising
providing a cell bandage according to claim 1 in intimate contact with the surfaces to be joined, wherein, after application of the cell bandage, cells are released from the cell bandage to bond the tissues together.

13. The method according to claim 12, wherein at least one of the tissues is cartilaginous and the cells are cartilage producing cells or cells capable of producing cartilage.

14. The method according to claim 12, wherein at least one of the tissues is transplanted or implanted cartilage and another is native cartilage at a recipient site.

15. The method according to claim 12, wherein at least one of the tissues is transplanted or implanted cartilage and another is bone at a recipient site.

16. The method according to claim 12, wherein the surfaces to be joined are formed by a fracture or tear in a tissue.

17. The method according to claim 16, wherein the tissues are meniscal cartilage and the surfaces to be joined are the surfaces formed by a meniscal tear.

18. The method according to claim 12, wherein said cell bandage promotes integration of transplanted or implanted cartilage and native cartilage at the site of surgical implantation.

* * * * *